(12) United States Patent  
Lee (10) Patent No.: US 10,060,794 B2
(45) Date of Patent: Aug. 28, 2018

(54) SPECTROMETER AND APPARATUS FOR MONITORING LIGHT-SHIELDED STATE

(71) Applicant: SAMSUNG ELECTRONICS CO., LTD., Suwon-si (KR)

(72) Inventor: June Young Lee, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 15/190,771

(22) Filed: Jun. 23, 2016

(65) Prior Publication Data

US 2016/0377481 A1 Dec. 29, 2016

(30) Foreign Application Priority Data

Jun. 24, 2015 (KR) .................. 10-2015-0089921

(51) Int. Cl.
| | | |
|---|---|---|
| *G01J 3/44* | (2006.01) | |
| *G01J 3/02* | (2006.01) | |
| *G01J 3/10* | (2006.01) | |
| *A61B 5/00* | (2006.01) | |

(52) U.S. Cl.
CPC .......... *G01J 3/0297* (2013.01); *A61B 5/0075* (2013.01); *A61B 5/441* (2013.01); *G01J 3/10* (2013.01); *G01J 3/4412* (2013.01); *A61B 2560/0406* (2013.01)

(58) Field of Classification Search
CPC .... G01J 3/0297; G01J 3/44; G01J 3/28; G01J 3/10; G01J 3/4412; A61B 5/0075; A61B 5/441; A61B 2560/0406; A61B 6/00; H01L 31/055; H01L 21/00

See application file for complete search history.

(56) References Cited

U.S. PATENT DOCUMENTS

| | | | |
|---|---|---|---|
| 5,115,138 A | * 5/1992 | Tanaka | G01J 1/58 250/372 |
| 7,362,426 B1 | 4/2008 | Yoo | |
| 2005/0248758 A1 | * 11/2005 | Carron | G01J 3/02 356/301 |
| 2007/0222982 A1 | 9/2007 | Tuschel et al. | |
| 2010/0091280 A1 | 4/2010 | Sano et al. | |

(Continued)

FOREIGN PATENT DOCUMENTS

| | | |
|---|---|---|
| JP | 2010-117343 A | 5/2010 |
| KR | 10-2004-0008903 A | 1/2004 |

(Continued)

*Primary Examiner* — Jamil Ahmed
(74) *Attorney, Agent, or Firm* — Sughrue Mion, PLLC (57) ABSTRACT

The spectrometer includes a spectrometer body; a shield including a layer on an exterior of the spectrometer body to prevent light from entering and escaping through an area other than a contact surface between the spectrometer body and an object; an internal light source placed within the shield and configured to emit light to the object; a spectroscope mounted in the spectrometer body and configured to allow the light that passes therethrough to be casted into a spectrum; a detector configured to have one surface that is in full contact with the spectroscope and to detect external light entering from outside of the shield; and a processor configured to, in response to the detector detecting the external light, perform a certain processing.

20 Claims, 9 Drawing Sheets

(56) References Cited

U.S. PATENT DOCUMENTS

| | | | |
|---|---|---|---|
| 2011/0001961 A1* | 1/2011 | Escuin Garcia | G08B 13/1445 |
| | | | 356/229 |
| 2011/0148834 A1* | 6/2011 | Baek | G09G 3/3406 |
| | | | 345/207 |
| 2012/0230669 A1* | 9/2012 | Abe | H01L 27/14618 |
| | | | 396/439 |
| 2016/0011111 A1* | 1/2016 | Stoll | G01N 21/645 |
| | | | 250/459.1 |

FOREIGN PATENT DOCUMENTS

| | | |
|---|---|---|
| KR | 10-2012-0098114 A | 9/2012 |
| KR | 10-2013-0099603 A | 9/2013 |
| WO | 2013/129755 A1 | 9/2013 |

\* cited by examiner

SPECTROMETER AND APPARATUS FOR MONITORING LIGHT-SHIELDED STATE

CROSS-REFERENCE TO RELATED APPLICATION

This application claims priority from Korean Patent Application No. 10-2015-0089921, filed on Jun. 24, 2015, in the Korean Intellectual Property Office, the disclosure of which is incorporated herein by reference in its entirety.

BACKGROUND

1. Field

Apparatuses and methods consistent with exemplary embodiments relate to improvement of an environment for a spectrometer to measure a spectrum.

2. Description of Related Art

Raman spectroscopy is a technique to identify a molecule. When the molecule is irradiated with a laser, the molecule absorbs energy as much as a difference between energy levels of electrons of the molecule, and based on the absorption, the molecule can be identified. Raman spectroscope analyzes elements of substance in a non-destructive way, and since each substance has its own Raman scattering spectrum, Raman spectroscope can analyze elements of a target substance from measured Raman scattering spectrum of the substance.

Generally, a Raman spectrum is measured in a light-shielded environment, such as a dark room, in an effort to reduce noise in the measurement. Any incoming external light may lead to an increase in noise, resulting in a reduced accuracy of measurement. In order to achieve a spectrum at a certain level of quality by using a Raman spectrometer, a dark room or a light-shielded environment is generally required, but such a limited environment may impose restrictions upon the measurement process.

Raman spectrometer may be used to analyze human skin, but a laser of the Raman spectrometer may harm the human body when it is discharged from the spectrometer. A high-power light source of several tens of mW is needed to detect a minute amount of elements in the human skin. If such a high-power light source is exposed outside of the spectrometer, and particularly, to human eyes, it may cause a burn to a cornea and/or retina or may cause a cataract, and hence a certain care is required in using the Raman spectrometer.

SUMMARY

Exemplary embodiments may address at least the above problems and/or disadvantages and other disadvantages not described above. Also, exemplary embodiments are not required to overcome the disadvantages described above, and may not overcome any of the problems described above.

One or more exemplary embodiments provide an apparatus and a method for improving a measurement environment for a spectrometer by monitoring whether the spectrometer is shielded from external light.

In accordance with an aspect of an exemplary embodiment, there is provided a spectrometer including: a spectrometer body; a shield including a layer on an exterior of the spectrometer body to prevent light from entering and escaping through an area other than a contact surface between the spectrometer body and an object; an internal light source placed within the shield and configured to emit light to the object; a spectroscope mounted in the spectrometer body and configured to allow light that passes therethrough to be casted into a spectrum; a detector configured to have one surface that is in full contact with the spectroscope and detect external light entering from outside of the shield; and a processor configured to, in response to the detector detecting the external light, perform predesignated processing.

The spectrometer may be a Raman spectrometer, the internal light source may be a monochromatic light source, and the spectroscope may be a Raman spectroscope that shows a spectrum of monochromatic light.

The detector may analyze a shape of spectrum incident through the contact surface to detect the external light.

The detector may analyze a type of the detected external light based on the shape of spectrum.

The type of the external light may include at least one of the following: natural light, an incandescent lamp, a fluorescent lamp, and a laser.

In response to an amount of external light detected being greater than a threshold, the processor may block the internal light source.

In response to the external light being detected, the processor may output an alarm or a warning sound to notify a user of whether an inside of the spectrometer is shielded from light.

The processor may provide a user with information about a specific reference spectrum that may occur when there is no external light.

In accordance with an aspect of an exemplary embodiment, there is provided a spectrometer including: a spectrometer body; a shield including a layer on an exterior of the spectrometer body to prevent light from entering and escaping through an area other than a contact surface between the spectrometer body and an object; an internal light source mounted within the shield and configured to emit light to the object; a spectroscope mounted in the spectrometer body and configured to allow light that passes therethrough to be casted into a spectrum; a detector configured to have one surface which includes a contact surface that is in contact with the spectroscope and a non-contact surface, and to detect external light incident from the outside of the shield; and a processor configured to, in response to the detector detecting the external light, perform predesignated processing.

The detector may detect external light from incoming light rays that have entered through the non-contact surface and the detector may analyze a type of the detected external light based on a shape of a spectrum incident through the contact surface.

In response to an amount of external light detected being greater than a threshold, the processor may block the internal light source.

In response to the external light being detected, the processor may output an alarm or a warning sound to notify a user of whether an inside of the spectrometer is shielded from light.

The processor may provide a user with information about a specific reference spectrum that may occur when there is no external light.

In accordance with an aspect of an exemplary embodiment, there is provided an apparatus for monitoring a light-shielded state of a spectrometer, the apparatus including: a light-shielded state analyzer configured to detect external light entering from outside of the spectrometer having a shield; and a monitoring device configured to perform designated processing in response to the external light being detected.

The light-shielded state analyzer may analyze a shape of spectrum incident through a spectroscope to detect the external light.

In response to the external light being detected, the light-shielded state analyzer may analyze a type of the external light.

The light-shielded state analyzer may detect the external light from light rays that have entered without passing through a spectroscope, and in response to the external light being detected, the light-shielded state analyzer may analyze the detected external light based on a shape of a spectrum incident through the spectroscope.

In response to an amount of external light detected being greater than a threshold, the monitoring device may block the internal light source.

In response to the external light being detected, the monitoring device may output an alarm or a warning sound to notify a user of whether an inside of the spectrometer is shielded from light.

The monitoring device may provide a user with information about a specific reference spectrum that may occur when there is no external light.

BRIEF DESCRIPTION OF THE DRAWINGS

The above and/or other aspects will become more apparent by describing certain exemplary embodiments with reference to the accompanying drawings, in which.

DETAILED DESCRIPTION

Certain exemplary embodiments will be described in greater detail with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

Figure 1:
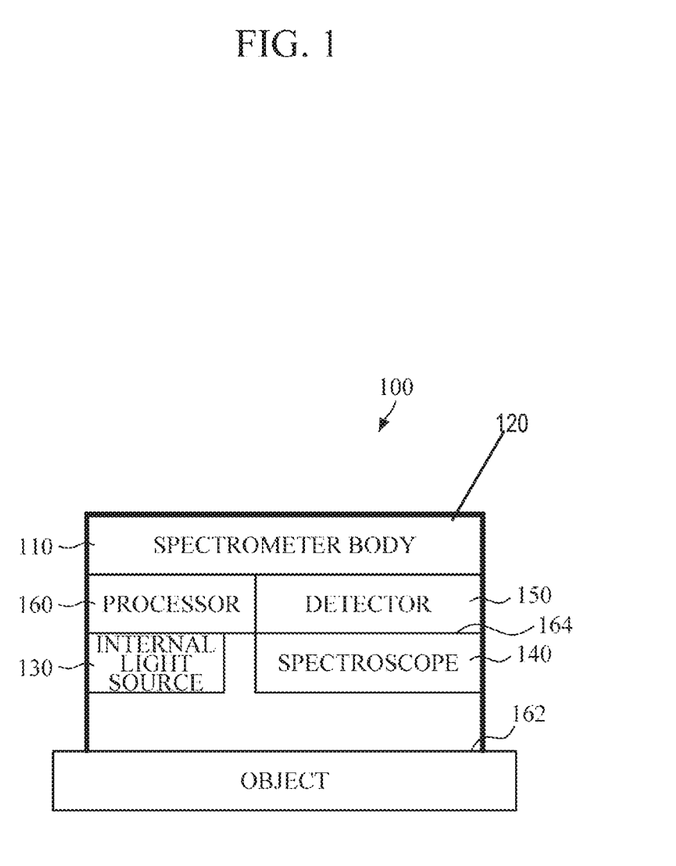
FIG. 1 is a diagram illustrating a configuration of a spectrometer according to an exemplary embodiment.

FIG. 1 is a diagram illustrating a configuration of a spectrometer according to an exemplary embodiment. Referring to FIG. 1, a spectrometer 100 includes a spectrometer body 110, a shield 120, an internal light source 130, a spectroscope 140, a detector 150, and a processor 160.

The spectrometer body 110 accommodates the internal light source 130, the spectroscope 140, the detector 150, and the processor 160.

The shield 120 is a layer on an exterior of the spectrometer body 110 to prevent the light from entering and escaping through an area other than a contact surface 162 between the spectrometer body 110 and an object. The shield 120 is a layer that separates the inside and outside of the spectrometer 100, preventing the internal light and the external light from entering and escaping. The shield 120 to prevent the entering and leaving of the internal light and external light is not provided on the contact surface 162 between the object and the spectrometer 100, and hence external light may enter into the spectrometer 100 during the measurement process. FIG. 1 illustrates the shield 120 formed on the external surfaces of the spectrometer 100, other than the contact surface in contact with the object. However, the shape, type, and size of the shield 120 are not limited to an exemplary embodiment described in FIG. 1.

The internal light source 130 within the shield 120 emits light to the object. The internal light source 130 may be light of a single wavelength, such as laser light, and a Raman spectrometer may use a laser as internal light.

The spectroscope 140 is mounted in the body 110, and light that passes through the spectroscope 140 is casted into a spectrum. At this time, the light incoming to the spectroscope 140 may include internal light irradiated by the internal light source 130 and external light incident from an external light source of the shield. If the spectrometer 100 is a Raman spectrometer, the spectroscope 140 may be a Raman spectroscope that shows the spectrum of monochromatic light.

For example, when the internal light source 130 emits monochromatic light to the object, scattered light enters into the spectroscope 140, and the spectroscope 140 casts the incoming light into a vibrational spectrum. At this time, if the external light enters into the spectroscope 140, a spectrum that has passed through the spectroscope 140 may appear to have been interfered by the external light.

The vibrational spectrum that has passed through the Raman spectroscope may be converted into an electrical signal through the detector 150, and the converted vibrational spectrum may be delivered to a user. The vibrational spectrum measured by the Raman spectrometer may be used to inspect vibrational structures of molecules or to perform qualitative, quantitative analysis of substance. Also, the Raman spectrometer may be used in research for an intracellular or extracellular biochemical, morphological information analysis on tissues.

The detector 150 having a contact surface 164, e.g., a first surface, that is in full contact with the spectroscope 140 detects external light incoming from the outside of the shield 120. Because the detector 150 detects the light that has passed through the spectroscope 140 and then comes into the detector 150, the detector 150 can detect both the internal and external light. The detector 150 may detect the external light by analyzing a spectrum of light incoming through the contact surface with the spectroscope 140.

According to the exemplary embodiment, when the spectrometer 100 is in close contact with the object and hence the external light is completely blocked by the shield 120, the detector 150 may detect analysis information of components existing in the object and separated into a spectrum.

If external light is introduced into a gap between the contact surfaces of the spectrometer 100 and the object, the vibrational spectrum that is incoming to the detector 150 contains the result of interference from the external light. Generally, CCD counts of external light is relatively greater than those of internal light, and hence when the external light has entered into the spectrometer, it is not possible to analyze the components of the object from the vibrational spectrum measured.

In the above case, the user has to perform again the measurement with the spectrometer 100. However, in some cases, the user may not notice that the measurement result is incorrect due to incoming external light. To prevent such an instance, once the detector 150 has detected external light, the processor 160 may perform necessary procedures to notify the user of the detection.

According to the exemplary embodiment, the detector 150 may analyze a shape of an incoming spectrum emitted through the contact surface in contact with the spectroscope 140 and detect external light based on the analysis result. For example, in the case where a laser that is monochromatic light is used the internal light source 130, the vibrational spectrum emitted into the detector 150 may cover a certain vibrational range. If there is incoming external light, the vibrational spectrum may have an irregular range or vibration counts that are out of a specific range. Examples of the vibrational spectrum will be described with reference to FIGS. 5 to 8.

The detector 150 may determine whether the external light has been introduced and analyze the type of external light source based on the shape of the vibrational spectrum. While the types of external light source may vary, types of external light sources that can be introduced to the spectrometer 100 in a common measurement environment may include natural light, an incandescent lamp, a fluorescent lamp, a laser, and the like. Because every external light has its own unique wavelength, the detector 150 may be able to analyze the type of external light source through the spectrum analysis.

As described above, the spectrum analysis process may be implemented through internal software or hardware configuration of the detector 150. However, the spectrum analysis process may also use external software or hardware configuration of the detector 150, and hence the implementation is not limited to the above-described.

Once the external light is detected by the detector 150, the processor 160 may perform designated processing. For example, if the amount of external light detected by the detector 150 is greater than a threshold, the processor 160 may block the internal light source 130. In order to measure the human skin condition, a high-power laser of several tens of mW is generally used. In the case where the internal light source 130 is a laser of the spectrometer, an externally exposed high-power laser may harm the user's health. If the detector 150 has detected the external light, it indicates that the spectrometer is not completely shielded, so the processor 160 may, in turn, block the internal light source 130.

In another example, once the external light has been detected, the processor 160 may output an alarm or a warning sound to notify the user of whether the inside of the spectrometer 100 is shielded from light, e.g., about a degree of adequate shielding. For example, the processor 160 provides information to notify the user that the inside of the spectrometer is not completely shielded from external light. A method of the processor 160 for notifying the user of whether the inside of the spectrometer is shielded may vary, and hence, exemplary embodiments are not limited to the above example.

In addition, the processor 160 may provide the user with information about a reference spectrum that may occur when there is no external light. Because a result the user wants to obtain is a spectrum measured in the condition where the external light is blocked, a spectrum that can be obtained in a proper measurement environment may be provided to the user as control data. In this case, the user may be able to estimate measurement results of the spectrometer from the reference spectrum.

FIG. 1 illustrates each element as a simple block. In addition to an exemplary embodiment described above, various arrangements of the elements are available, and aspects of the exemplary embodiment of FIG. 1 are not limited in a size, shape, and disposition of each element.

Figure 2A:
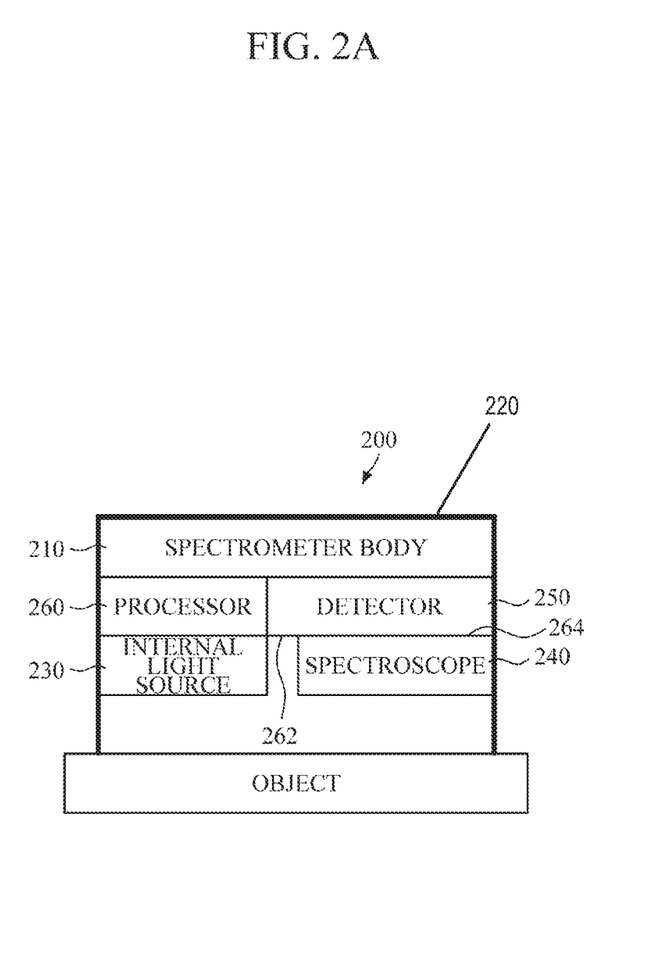
FIG. 2A is a diagram illustrating a configuration of a spectrometer according to another exemplary embodiment.
Figure 2B:
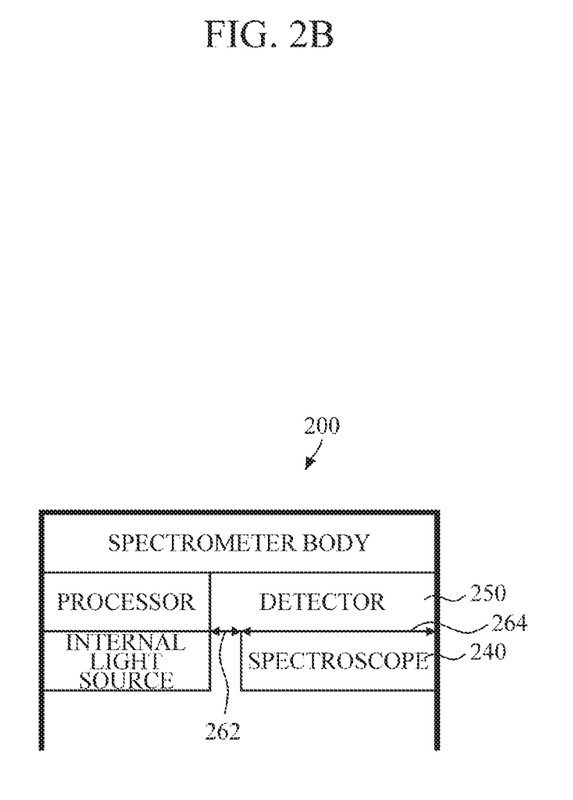
FIG. 2B is a diagram showing an example of a contact surface and a non-contact surface between the detector and the spectroscope.

FIG. 2A is a diagram illustrating a configuration of a spectrometer according to another exemplary embodiment. FIG. 2B is a diagram showing an example of a contact surface and a non-contact surface between the detector and the spectroscope.

Referring to FIG. 2A, a spectrometer 200 includes a spectrometer body 210, a shield 220, an internal light source 230, a spectroscope 240, a detector 250, and a processor 260. Here, the spectrometer body 210, the shield 220, the internal light source 230, the spectroscope 240, the detector 250, and the processor 260 are already described with reference to FIG. 1, and hence the descriptions thereof will be omitted.

The detector 250 which has one surface consisting of a contact portion 264 (hereinafter, will be referred to as a "contact surface") that is in contact with the spectrometer; and the remaining non-contact portion 262 (hereinafter, will be referred to as a "non-contact surface") detects external light introduced into the spectrometer 200. Referring to FIG. 2B, arrows denote the contact surface between the detector 250 and the spectroscope and the non-contact surface, respectively. Positions or arrangement of the detector 250 and the spectroscope 240 are not limited to an exemplary embodiment shown in FIG. 2B, such that any portion of the detector 250 which is not in contact with the spectroscope, but can detect light scattered from the object, can be a non-contact surface.

Detection of light that has entered through the contact surface may be less sensitive than the detection of light that has entered through the non-contact surface. Because the non-contact surface has a high sensitivity to light, a low intensity or a small amount of incoming external light can be detected through the non-contact surface.

For example, the detector 250 may detect external light from the incoming light rays that have passed through the non-contact surface, and analyze a type of external light source based on the shape of incoming spectrum emitted through the contact-surface between the detector 250 and the spectroscope 240. The detector 250 may detect external light from among incoming light rays that have passed through the non-contact surface which has a high sensitivity to light, and if the external light is not detected, the detector 250 may not carry out the analysis of the shape of incoming spectrum emitted through the contact surface in contact with the spectroscope 240. In addition, when the detector 250 detects the external light through the non-contact surface, it is possible to detect a smaller amount or a lower intensity of external light, as compared to when detecting the external light only through the contact surface in contact with the spectroscope 240.

In another example, the detector 250 may analyze the shape of incoming spectrum emitted through the contact surface in contact with the spectroscope, and then detect external light based on the analysis result. If the internal light source 230 uses a single laser, the vibrational spectrum that is emitted into the detector 250 may cover a certain vibrational range. If there is incoming external light, the vibrational spectrum may have an irregular range or vibration counts that are out of a specific range. Examples of the vibrational spectrum will be described with reference to FIGS. 5 to 8.

The detector 250 may analyze the type of external light source based on the shape of vibrational spectrum. Examples of the light source may include natural light, incandescent lamp, fluorescent lamp, laser, and the like. Because every external light has its own unique wavelength, the detector is able to analyze the type of external light source using the spectrum analysis.

In addition, the detector 250 converts the spectrum of the detected light into an electrical signal and makes a record of the electrical signal, thereby allowing the spectrum that has passed through the spectroscope to be provided as information that can be delivered to the user.

The spectrum analysis process as described in the above examples may be implemented through internal software or hardware configuration of the detector 250. However, the spectrum analysis process may also use external software or hardware configuration of the detector 150, and hence the implementation is not limited to the above-described.

Figure 3:
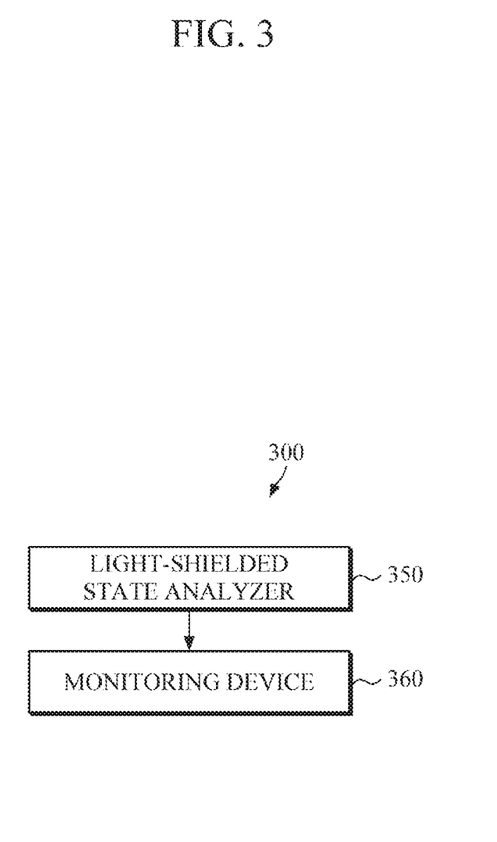
FIG. 3 is a diagram illustrating an apparatus for monitoring whether a spectrometer is shielded from light, according to an exemplary embodiment.

FIG. 3 is a diagram illustrating an apparatus for monitoring whether a spectrometer is shielded from light, according to an exemplary embodiment. An apparatus 300 for monitoring whether a spectrometer is shielded from light may include a light-shielded state analyzer 350 and a monitoring device 360. Here, the spectrometer may be a Raman spectrometer that has a monochromatic light source as an internal light source and measures a spectrum of the monochromatic light.

The light-shielded state analyzer 350 may detect external light that enters from the outside of a shield of the spectrometer, and then may analyze the detected light. The spectrometer has the shield to prevent external light and internal light from being entering and escaping. However, a contact surface between the spectrometer and an object is not provided with the shield, and hence external light can enter through the contact surface into the spectrometer during measurement of the object.

For example, the light-shielded state analyzer 350 may analyze a shape of incoming spectrum emitted through the spectroscope to detect external light. For example, if a laser that is a monochromatic light source is used as an internal light source, a vibrational spectrum emitted into a detector may cover a certain vibrational range. If there is incoming external light, the vibrational spectrum may have an irregular range or vibration counts that are out of a specific range. The light-shielded state analyzer 350 may analyze whether external light has been introduced or the type of external light source based on the shape of vibrational spectrum which has passed through the spectroscope.

Once the light-shielded state analyzer 350 detects external light, it may analyze the type of external light source. The types of external light source may include at least one of natural light, incandescent lamp, fluorescent lamp, laser, and the like.

In another example, the light-shielded state analyzer 350 may detect external light from among light rays entering without passing through the spectroscope, and if the external light is indeed detected, the light shielded state analyzer 350 may analyze the detected external light based on the shape of the incoming spectrum that has passed through the spectroscope.

For example, the light-shielded state analyzer 350 may detect the external light by comparing the range of counts represented in the detected vibrational spectrum to a specific range of counts that the vibrational spectrum of internal light may have. In this case, because the light-shielded state analyzer 350 detects the external light from the incoming light that has not passed through the spectroscope, the sensitivity to light may be relatively higher, and hence it is possible to detect a small amount or a low intensity of external light.

If external light is detected from incoming light that has not passed through the spectroscope, the light-shielded state analyzer 350 may analyze the detected external light based on the shape of incoming spectrum that has passed through the spectroscope. At this time, the light-shielded state analyzer 350 may analyze the type of external light source based on the shape of spectrum. Examples of the external light source may include natural light, incandescent lamp, fluorescent lamp, laser, and the like. Because every external light has its own unique wavelength, the light-shielded state analyzer 350 is able to analyze the type of external light source using the spectrum analysis.

In this case, the light-shielded state analyzer 350 may be a software or hardware configuration in the spectrometer.

The monitoring device 350 may perform designated processes when the light-shielded state analyzer 350 has detected the external light. When an amount of external light detected is greater than a threshold, the monitoring device 360 may cut off the internal light source. In order to measure the human skin condition, a high-power laser of several tens of mW is generally used. In the case where the internal light source of the spectrometer is a laser, an externally exposed high-power laser may harm the user's health. If the external light is detected, it indicates that the spectrometer is not completely shielded, so the monitoring apparatus 350 may, in turn, block the internal light source.

In another example, the monitoring device 360 may output an alarm or a warning sound to notify the user of whether the inside of the spectrometer is shielded from light. The monitoring device 360 provides information to notify the user that the inside of the spectrometer is not completely shielded from external light. A method of the monitoring device 360 for notifying the user of whether the inside of the spectrometer is shielded may vary, and hence, exemplary embodiments are not limited to the above example.

In addition, the monitoring device 360 may provide the user with information about a reference spectrum that may occur when there is no external light. Because a result the user wants to obtain is a spectrum measured in the condition where the external light is blocked, a spectrum that can be obtained in a proper measurement environment may be provided to the user as control data. In this case, the user may be able to estimate measurement results of the spectrometer from the reference spectrum.

As described above, the monitoring device 360 may monitor in real time whether the inside of the spectrometer is shielded or not, and may control the spectrometer according to the monitoring result.

Figure 4:
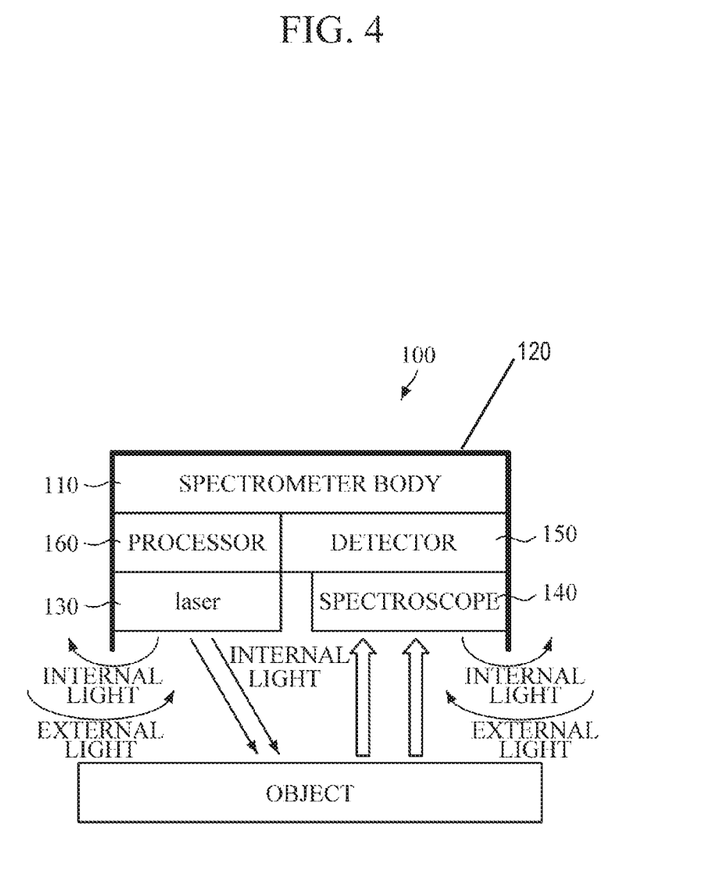
FIG. 4 is a diagram illustrating incoming and outgoing of internal and external light in a spectrometer according to an exemplary embodiment.

FIG. 4 is a diagram illustrating incoming and outgoing of internal and external light in a spectrometer according to an exemplary embodiment. According to the exemplary embodiment, it is required that a Raman spectrometer uses monochromatic light as an internal light source and the measurement is carried out in a darkroom in order obtain accurate measurement results. Even a minute amount of external light may interfere with the spectrum, thereby affecting the measurement results.

A spectrometer body 110 blocks the external light by using a shield 120. However, the contact surface of the spectrometer in contact with an object cannot be shielded by the shield 120, and therefore a gap may exist between the spectrometer and the object.

Referring to FIG. 4, if the object is human skin and a gap between the spectrometer and the skin is not completely shielded, external light may be emitted into the spectrometer while internal light irradiated from the laser, which is the internal light source of the spectrometer, may escape from the gap.

When the laser 130 which is the internal light source emits light to the skin, the emitted internal light is scattered from the skin, and parts of scattered light enter through the spectroscope 140. Light that has passed through the spectroscope 140 is emitted into the detector 150 in a vibration spectrum, and the detector 150 detects the incoming light and converts the detected light into an electrical signal. At this time, if the external light enters into the spectrometer as shown in FIG. 4, the detector 150 may detect the external light and performs designated process using a processor.

According to the exemplary embodiment, the spectrometer 100 can analyze the type of external light based on the shape of the vibrational spectrum. Hereinafter, the shape of vibrational spectrum that is measured in the presence and absence of external light, and according to the type of external light will be described with reference to FIGS. 5 to 7.

Figure 5:
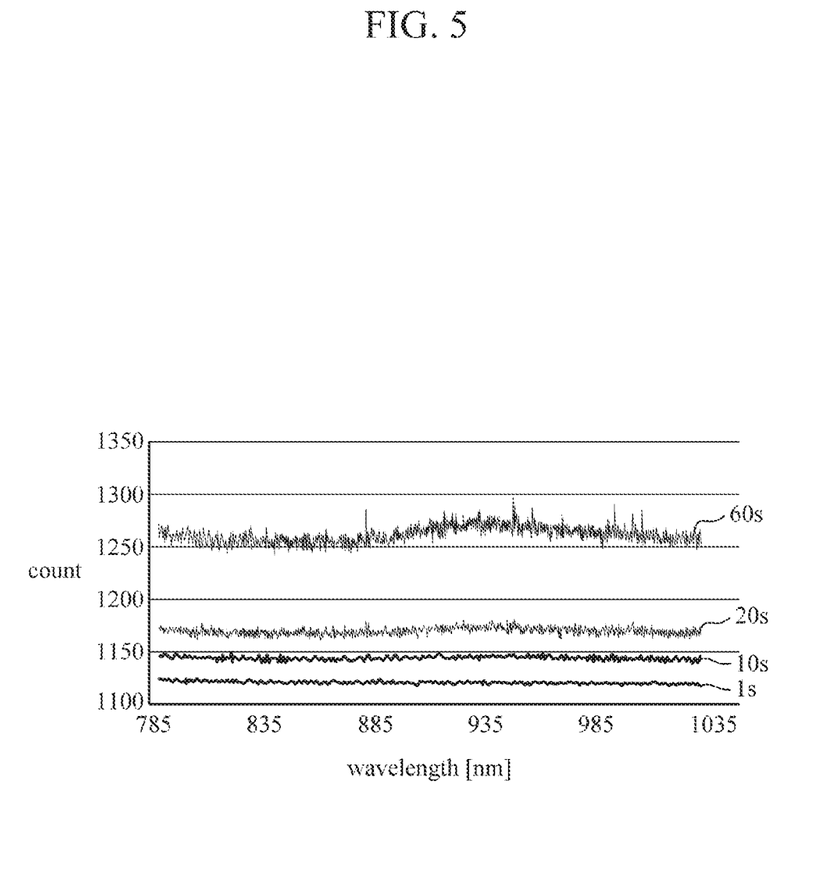
FIG. 5 is a graph illustrating examples of a spectrum measured in an environment where the external light is blocked.

FIG. 5 is a graph illustrating examples of a spectrum measured in the environment where the external light is blocked. The x-axis represents a wavelength (nm) and the y-axis represents counts (CCD counts) due to vibration. According to the exemplary embodiment, the Raman spectrometer emits a laser, which is monochromatic light, to an object, and a vibrational spectrum of the object that has passed through a spectroscope remains within a relatively constant range.

For example, a graph of FIG. 5 shows vibrational spectra measured for different periods, i.e., 1 second, 10 seconds, 20 seconds, and 60 seconds. As the time period for measurement increases, the measured counts also increase, while each vibration spectrum remains within a specific range of counts because the light incident into the Raman spectroscope is monochromatic light.

Figure 6:
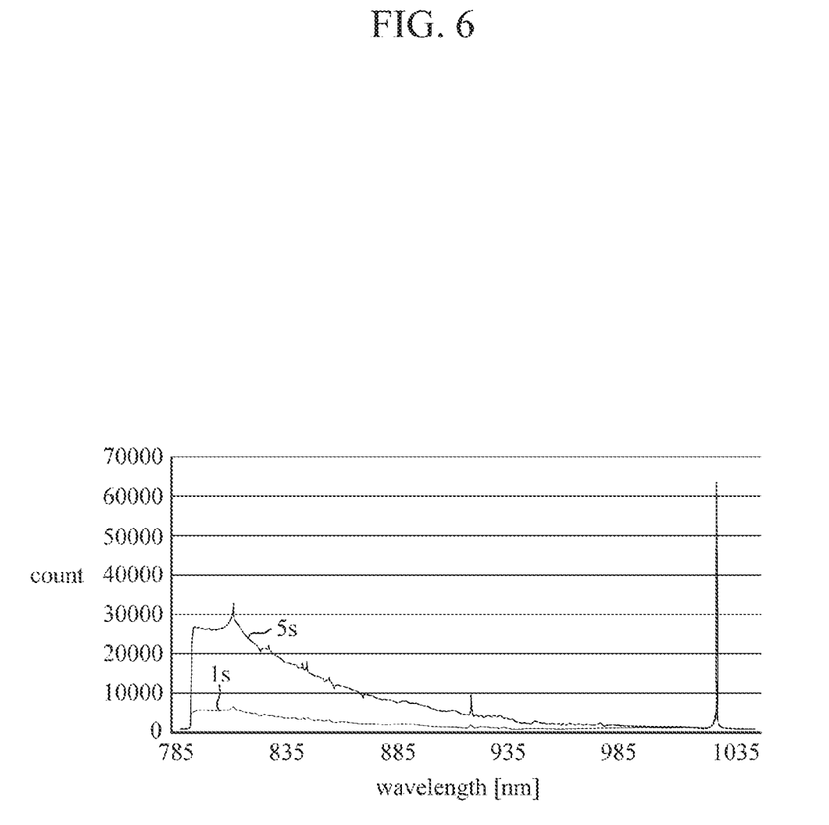
FIG. 6 is a graph showing examples of a spectrum measured when external light has been introduced.

FIG. 6 is a graph showing examples of a spectrum measured when external light has been introduced. The graph of FIG. 6 shows the influence of incoming external light that on the spectrum measurement of the spectroscope. When the external light enters into the spectroscope, a probability of noise occurring increases, and if the external light is not monochromatic light, such as a laser, counts may fluctuate widely depending on wavelengths. Referring to FIG. 6, count values corresponding to wavelengths between 785 nm up to 935 nm vary drastically. Also, it is seen that the count value increases up to 30000, which indicates the range of count values increases as compared to the spectra of FIG. 5, which are measured in a light-shielded environment.

Measurement results obtained in the presence of incoming external light, as shown in FIG. 6, may be significantly different from the results obtained in the presence of internal light only, and noise caused by the external light may lead to a high peak at a specific wavelength. According to the exemplary embodiment, the vibrational spectra differ depending on the presence of internal light only, or both internal and external light, and thus, the spectrometer is able to analyze whether the external light has been detected by analyzing the shape of the spectrum. In this case, because counts due to the internal light are negligible compared to the counts due to the external light, any incoming external light may significantly affect the measurement results.

Figure 7:
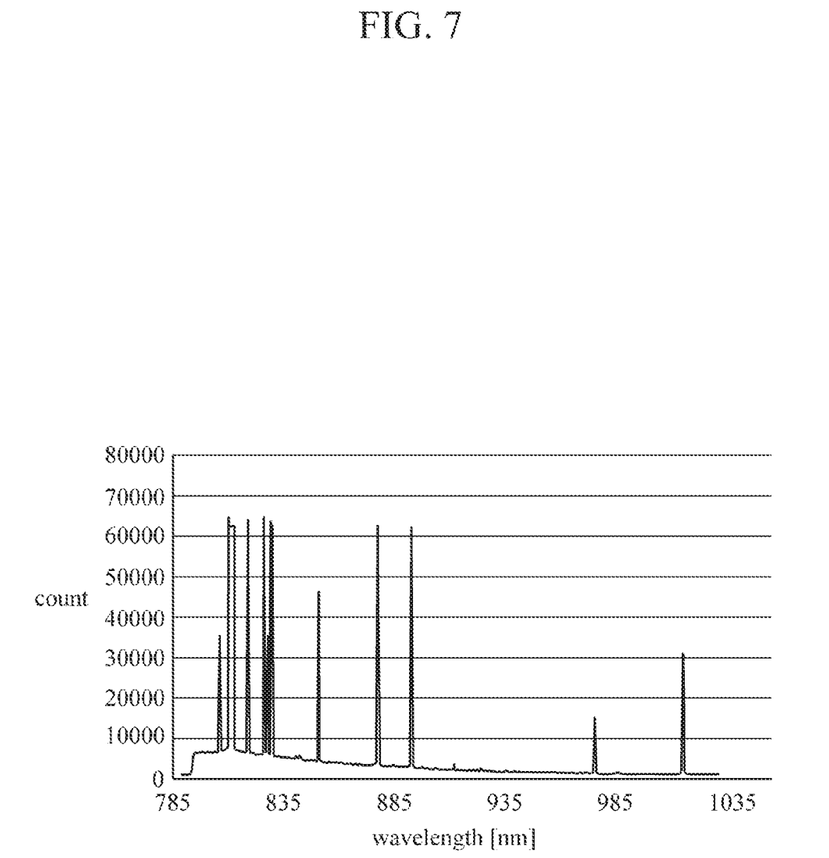
FIG. 7 is an example of a vibrational spectrum measured when a type of incident external light is fluorescent light.
Figure 8:
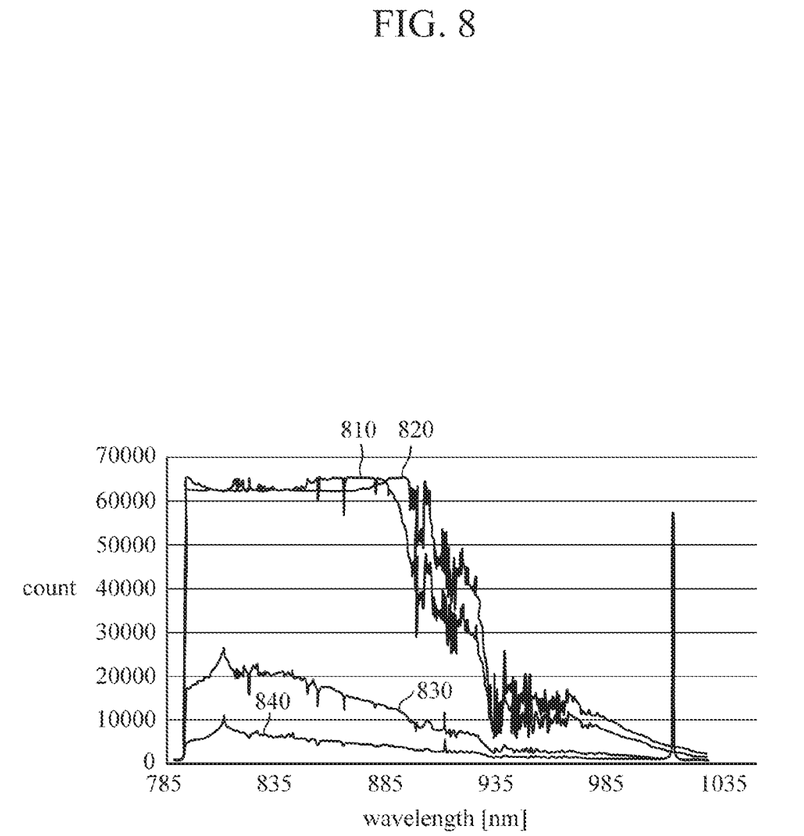
FIG. 8 is an example of vibrational spectra measured when a type of incident external light is natural light.

FIGS. 7 and 8 are graphs showing shapes of vibrational spectra according to types of external light. FIG. 7 is an example of a vibrational spectrum measured when a type of incident external light is fluorescent light. Referring to FIG. 7, in the case where fluorescent light is the incoming external light, it is observed that a number of narrow peaks occur at specific wavelengths. Hence, if a vibrational spectrum measured by a spectrometer exhibits a shape having several peaks at the specific wavelengths, as shown in the graph of FIG. 7, the type of external light may be determined to be fluorescent light.

FIG. 8 is an example of vibrational spectra measured when a type of incident external light is natural light. Natural light has a wide spectral range from infrared (IR) over the visible up to the ultraviolet (UV) range, and thus it can affect a wide range of the spectrum.

Shown in FIG. 8 are examples of a spectrum that are measured for the same length of time but with different light intensity. In FIG. 8, graph 810 and graph 820 each have count values of more than 60000 at specific wavelength bands, from which it may be inferred that the vibrational spectrum was measured under natural light of high intensity in a relatively bright environment.

In a similar manner, it may be analyzed that a vibrational spectrum of graph 830 having count values of more than 20000 at specific wavelength bands was measured in a relatively dimmer environment compared to the environment where vibrational spectra of graphs 810 and 820 were measured. In addition, it is seen that graph 840 shows count values of about less than 10000 at almost any wavelength, and based on the range of count values measured, it may be analyzed that a vibrational spectrum of graph 840 was measured in a shaded or dark environment.

As such, the spectrometer may analyze the shape of vibrational spectrum to determine the type of external light, and also may analyze the counts of vibrational spectrum to determine the light intensity of the measurement environment.

As seen in comparison between graphs of FIGS. 7 and 8, fluorescent light has a graph form that is clearly different from that of natural light, and thus, the spectrometer may be able to analyze the type of incoming external light based on each spectrum.

The exemplary embodiments can be implemented as computer readable codes in a computer readable record medium. Codes and code segments constituting the computer program can be easily inferred by a skilled computer programmer in the art. The computer readable record medium includes all types of record media in which computer readable data are stored. Examples of the computer readable record medium include a ROM, a RAM, a CD-ROM, a magnetic tape, a floppy disk, and an optical data storage. Further, the record medium may be implemented in the form of a carrier wave such as Internet transmission. In addition, the computer readable record medium may be distributed to computer systems over a network, in which computer readable codes may be stored and executed in a distributed manner.

Although a few exemplary embodiments have been shown and described, exemplary embodiments are not limited thereto. It would be appreciated by those skilled in the art that changes may be made in these exemplary embodiments without departing from the principles and spirit of the disclosure, the scope of which is defined in the claims and their equivalents.

What is claimed is:

1. A spectrometer comprising:
   a spectrometer body;
   a shield comprising a layer on an exterior of the spectrometer body to prevent light from entering and escaping through an area other than a contact surface between the spectrometer body and an object;
   an internal light source placed within the shield and configured to emit light to the object;
   a spectroscope mounted in the spectrometer body and configured to allow light that passes therethrough to be casted into a spectrum;
   a detector, which has a first surface, an entirety of which is in full physical contact with the spectroscope, and a non-contact portion which is not in physical contact with the spectroscope, and which is configured to detect an external light entering from an outside of the shield; and
   a processor configured to perform a certain processing, in response to the detector detecting the external light.

2. The spectrometer of claim 1, wherein the internal light source includes a monochromatic light source, and
   the spectroscope includes a Raman spectroscope that shows a spectrum of a monochromatic light.

3. The spectrometer of claim 1, wherein the detector is configured to analyze a shape of the spectrum transmitted through the first surface to detect the external light.

4. The spectrometer of claim 3, wherein the detector is configured to analyze a type of the detected external light based on the shape of the spectrum.

5. The spectrometer of claim 4, wherein the type of the external light comprises at least one among a natural light, an incandescent lamp light, a fluorescent lamp light, and a laser light.

6. The spectrometer of claim 1, wherein the processor is configured to block the internal light source, in response to an amount of the detected external light being greater than a threshold.

7. The spectrometer of claim 1, wherein the processor is configured to output an alarm or a warning sound to notify a user of a degree to which an inside of the spectrometer is shielded from the external light, in response to the external light being detected.

8. The spectrometer of claim 1, wherein the processor is configured to provide a user with information about a specific reference spectrum that may occur when there is no external light being detected.

9. A spectrometer comprising:
   a spectrometer body;
   a shield comprising a layer on an exterior of the spectrometer body to prevent a light from entering and escaping through an area other than a contact surface between the spectrometer body and an object;
   an internal light source mounted within the shield and configured to emit light to the object;
   a spectroscope mounted in the spectrometer body and configured to allow the light that passes therethrough to be casted into a spectrum;
   a detector, which has a first surface which comprises a contact portion that is in physical contact with the spectroscope and a non-contact portion which is not in physical contact with the spectroscope, and is configured to detect external light transmitted from an outside of the shield; and
   a processor configured to perform a certain processing, in response to the detector detecting the external light.

10. The spectrometer of claim 9, wherein the detector is configured to detect the external light from incoming light rays that have entered through the non-contact portion of the first surface, and the analyze a type of the detected external light based on a shape of the spectrum transmitted through the contact portion of the first surface.

11. The spectrometer of claim 9, wherein the processor is configured to block the internal light source, in response to an amount of the external light detected being greater than a threshold.

12. The spectrometer of claim 9, wherein the processor is configured to output an alarm or a warning sound to notify a user of a degree to which an inside of the spectrometer is shielded from the external light, in response to the external light being detected.

13. The spectrometer of claim 9, wherein the processor is configured to provide a user with information about a specific reference spectrum that may occur when there is no external light being detected.

14. An apparatus for monitoring a light-shielded state of a spectrometer, the apparatus comprising:
   a light-shielded state analyzer configured to detect an external light entering from an outside of the spectrometer being shielded with a shield, the shield comprising a layer on an exterior of a spectrometer body of the spectrometer to prevent light from entering and escaping through an area other than a contact surface between the spectrometer body and an object; and
   a monitoring device configured to perform a certain processing in response to the external light being detected,
   wherein the external light is detected by a detector having a first surface in full physical contact with a spectroscope, and a non-contact portion which is not in physical contact with the spectroscope.

15. The apparatus of claim 14, wherein the light-shielded state analyzer is configured to analyze a shape of a spectrum incident on a spectroscope to detect the external light.

16. The apparatus of claim 15, wherein the light-shielded state analyzer is configured to analyze a type of the external light based on the shape of the spectrum, in response to the external light being detected.

17. The apparatus of claim 14, wherein the light-shielded state analyzer is configured to detect the external light from light rays that have entered without passing through a spectroscope, and analyze the external light based on a shape of a spectrum incident on the spectroscope, in response to the external light being detected.

18. The apparatus of claim 14, wherein the monitoring device is configured to block the internal light source, in response to an amount of the detected external light being greater than a threshold.

19. The apparatus of claim 14, wherein the monitoring device is configured to output an alarm or a warning sound to notify a user of a degree to which an inside of the spectrometer is shielded from the external light, in response to the external light being detected.

20. The apparatus of claim 14, wherein the monitoring device is configured to provide a user with information about a specific reference spectrum that may occur when there is no external light being detected.

* * * * *